United States Patent [19]
Wogoman

[11] Patent Number: 5,089,417
[45] Date of Patent: Feb. 18, 1992

[54] FLUID SEPARATION AND PROCESSING DEVICE

[75] Inventor: Frank W. Wogoman, South Bend, Ind.

[73] Assignee: Miles Inc., Elkhart, Ind.

[21] Appl. No.: 461,495

[22] Filed: Jan. 5, 1990

Related U.S. Application Data

[62] Division of Ser. No. 68,451, Jul. 1, 1987, Pat. No. 4,892,702.

[51] Int. Cl.[5] .................... G20L 31/00; G20L 21/00
[52] U.S. Cl. ................................. 436/45; 436/177; 436/63; 210/787; 210/789
[58] Field of Search ........... 422/64, 102, 72, 100, 422/104; 436/63, 45, 177; 210/787, 789

[56] References Cited

U.S. PATENT DOCUMENTS 4,814,282 3/1989 Holen ................................. 436/165

Primary Examiner—David L. Lacey
Assistant Examiner—David Redding
Attorney, Agent, or Firm—Roger N. Coe

[57] ABSTRACT

An assembly for separating, metering and delivering fluids such as whole blood, includes a central rotating member rotatable about a fixed spin axis. A processing chamber holding member is connected to the central rotating member by a centrifugally actuated frame. At rotational speeds below a first predetermined speed, the centrifugally actuated frame is in a first position. At rotational speeds greater than the first speed, centrifugal force moves the frame to a second position angularly spaced from and at greater distance from the spin axis than the first position. A processing chamber is mounted on the holding member and its orientation relative to the spin axis is the same in the first and second positions. Fluid is provided in the processing chamber. By accelerating the processing chamber to the first predetermined speed and decelerating below the first predetermined speed in a selected sequence, specific centrifugal force vectors are generated in the processing chamber that move the fluid and retain it in selected chambers. During this sequence, the fluid is metered, separated and delivered to a reduction area where measuring is performed.

3 Claims, 3 Drawing Sheets

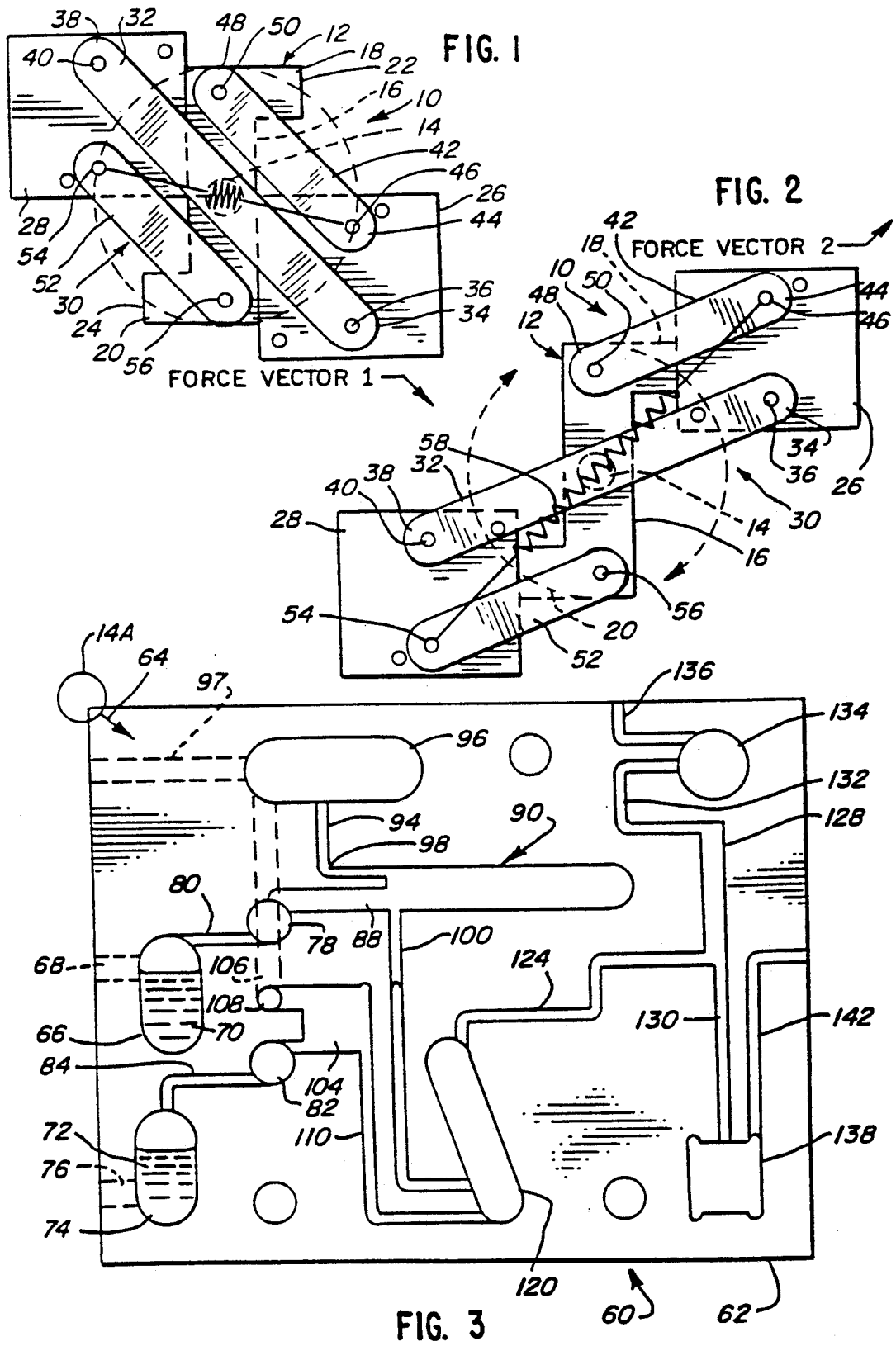

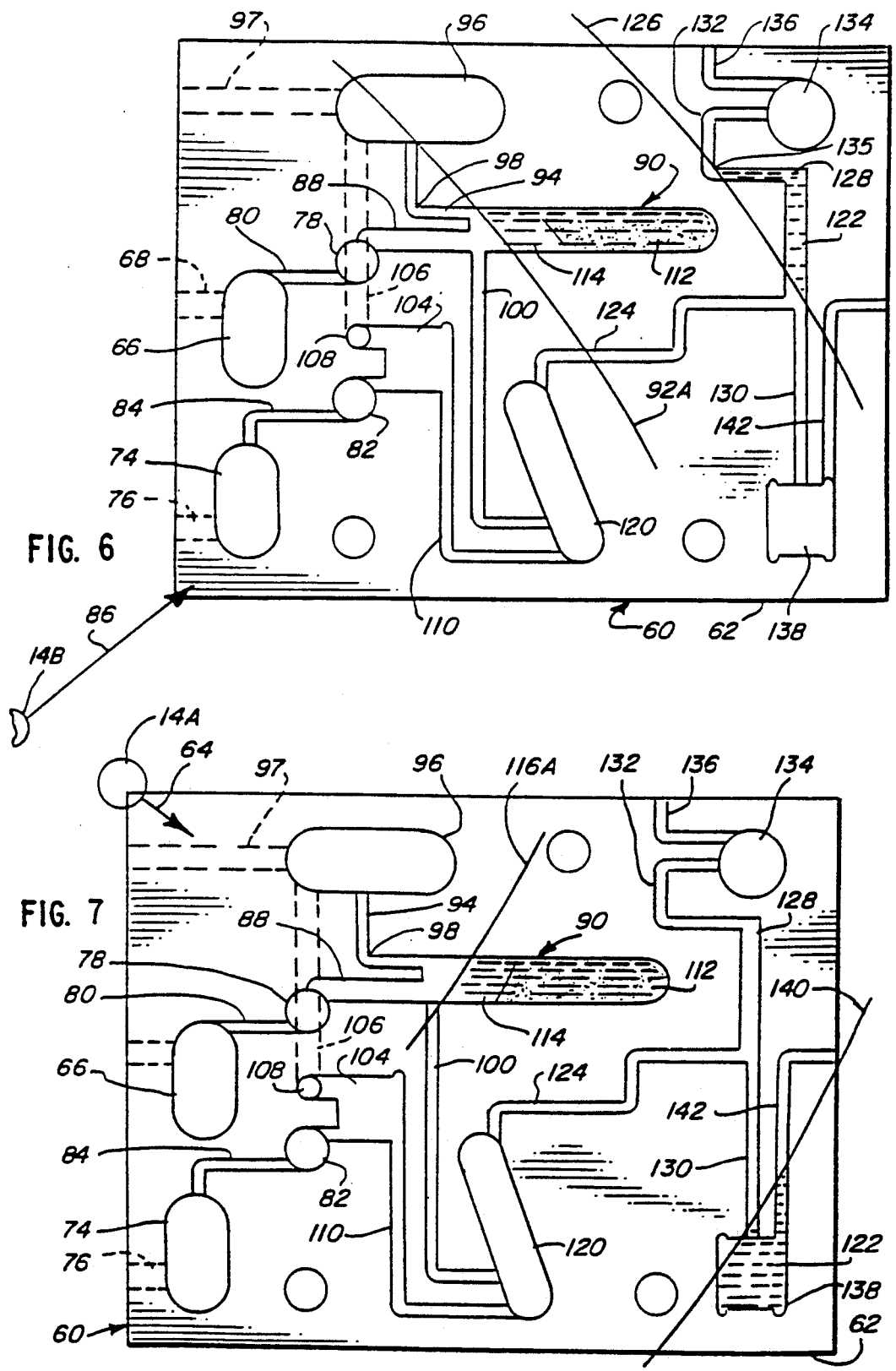

FLUID SEPARATION AND PROCESSING DEVICE

This is a division of application Ser. No. 68,451, filed on July 1, 1987, now U.S. Pat. No. 4,892,708.

BACKGROUND OF THE INVENTION

A. Field Of The Invention

The present invention relates to fluid separation devices and planchettes or processing chambers therefor, and more particularly, the present invention relates to a centrifugally actuated device that can apply different centrifuge force vectors on the planchette to control fluid flow within the planchette. The invention is particularly applicable to the processing of whole blood.

B. Descrietion of the Backqround Art

Analysis of fluids is required in a wide variety of instances. One common analysis is to determine blood chemistries. This analysis involves obtaining a sample of blood from a patient and centrifuging the blood sample to separate solid components such as, for example, red blood cells from the liquid component of the blood sample. Upon separating the liquid component, it is metered, diluted with a buffer solution and applied to a reagent for measuring. This analysis requires a number of time consuming, manual steps and the use of elaborate and complex instrumentation.

Manual analyses require obtaining a blood sample and placing it into a centrifuge device to obtain liquid separation from the solid components. The liquid is then manually removed and transferred to a container for dilution and/or mixing with reagents Once mixing has occurred, an instrument is used to measure the different components in the sample. In an attempt to eliminate these manual steps, several instruments have been developed that use centrifugal force to perform the various analyses while minimizing the need for manual manipulation. One such instrument is disclosed in European patent application 160,901, filed Apr. 26, 1985. This application discloses an apparatus for generating centrifugal force and includes a plate rotatable about an axis with at least one holding device mounted on the plate. The holding device is adapted to receive a processing card or planchette. The apparatus includes structure for rotating the planchette relative to the plate member during spinning of the plate member thereby changing the portion of the processing card acted on by the centrifugal force. In this apparatus, the planchette or processing card remains in the same location relative to the plate member; however, the processing card or planchette is rotated such that different sides or ends of the planchette are acted on by the centrifugal force vector.

The apparatus described in European Patent Application No. 160,901 requires complex mechanical structure and related equipment in order to accomplish the rotation of the planchette or processing card during spinning of the plate. The complexity of the mechanical structure required increases the expense of the apparatus and servicing of the apparatus is expensive and difficult. Moreover, the apparatus is very sensitive to balancing since if it is slightly out of balance, the vibration can damage or destroy the complex mechanical structure.

In centrifugal analysis devices of the type described, the processing card or planchette is also very important. An example of a processing card or planchette is provided in European patent application 160,282, filed Apr. 26, 1985. This application discloses a sample processing card or planchette that is to be used with a centrifuge device. The processor card or planchette includes a supply of chemical reagent and inlet means for supplying a chemical sample such as whole blood into the processing card. The chemical sample is moved by centrifugal force through different passages and chambers in the processing card and is mixed with a reagent allowing a chemical analysis to be performed.

The disclosed processing card or planchette requires overflow chambers and cavities to provide the desired measured amount of fluid. This processing card relies on a true fill and emptying process wherein the different chambers and cavities are filled and the processing card is physically rotated to empty fluid out of the different chambers and cavities. Physical barriers in the form of walls partially extending into openings in the chamber are necessary to prevent the emptying of separated material out of the cavities when the processing.card is rotated. For example, whole blood may be centrifuged in one of the cavities. The processing card is then rotated relative to a plate of the centrifuge to pour plasma out of the cavity while the solid red blood cells are held in the cavity by a barrier wall at the mouth of the cavity. Since the cavities are physically filled or emptied in accordance with this process, the location of the processing card relative to the spin axis of the centrifuge device is not critical.

It is desirable to provide an apparatus for performing chemical analyses using centrifugal force that has a minimum of mechanical structural elements thereby simplifying the apparatus, reducing its cost and allowing quick and easy servicing. In addition, a processing card or planchette without physical barriers thereby simplifying its construction is also desirable.

SUMMARY OF THE INVENTION

An object of the present invention is to provide a new and improved apparatus for performing chemical analyses on fluids such as whole blood.

Another object of the present invention is to provide a new and improved planchette that can be used with a centrifuge device to perform chemical analyses on fluids such as whole blood.

Another object of the present invention is to provide a new and improved method for separating, metering, diluting and delivering a fluid such as whole blood for chemical analyses.

A still further object of the present invention is to provide a new and improved centrifuge apparatus for separating, metering, diluting and delivering a fluid for chemical analyses in a planchette that uses specific centrifugal force vectors to move the fluid and a curved fluid line produced by the centrifugal force to hold it within selected chambers in the planchette.

Still another object of the present invention is to provide a new and improved apparatus that translates a planchette from a first angular position to a second angular position relative to a spin axis of the apparatus to apply different centrifugal force vectors on the planchette.

Another object of the present invention is to provide a new and improved planchette that does not require physical barriers to control the flow of fluids and solids through the planchette.

Briefly, the present invention is directed to a new and improved assembly or device for separating, metering, diluting and delivering a fluid such as whole blood for chemical analyses, to a new and improved method for separating, metering, diluting and delivering a fluid for chemical analyses, and to a new and improved planchette. The new and improved assembly can be used to separate plasma and red blood cells in a sample of whole blood and perform one of several different chemical analyses such as a testing for glucose.

The assembly includes a centrifuge device with a rotating member rotatable about a fixed spin axis. A planchette holding member is moved around the spin axis by a centrifugally actuated frame. The frame is biased to a first position by a spring or similar element during start-up of the assembly. Upon the assembly reaching a first predetermined spin speed, centrifugal force overcomes the biasing force of the spring translating the frame to a second position. This action by the frame moves the planchette holding member to a second position spaced angularly from the first position and radially farther from the spin axis than the first position. Orientation of the planchette holding member, however, does not change relative to the spin axis in the first and second positions.

In order to perform any of a number of chemical analyses, a planchette with unobstructed cavities and passages is provided. A sample of fluid to be analyzed, such as whole blood, can be introduced into the planchette along with a buffer into separate fill chambers. During start-up of the centrifuge device, the centrifugal force vector moves from a start-up position to a spin speed position. Upon reaching spin speed, the frame, under the influence of centrifugal force, translates the planchette from a first position to a second position. As this occurs, the centrifugal force vector acting on the planchette translates from a first angular position to a second angular position. Centrifugal force acting on the planchette along the second force vector moves the whole blood and the buffer solution from the fill chambers through passages into separate, open metering chambers. During rotation of the centrifugal device, a curved fluid fill line is formed in the metering chambers. The metering chambers are located on the planchette to be a predetermined distance from the spin axis such that the fluid fill line acts as a barrier to the flow of buffer and blood from their respective metering chambers and meters the blood and buffer to predetermined volumes.

The assembly is rotated at the spin speed for a predetermined period of time to separate red blood cells from plasma. Once separation is accomplished, the assembly is decelerated. As this occurs, the spring overcomes the centrifugal force translating the frame and the planchette from the second position to the first position. In both the first and second positions, the orientation of the planchette relative to the spin axis remains the same. As the planchette returns to the first position, the centrifuge force vector acting on the planchette returns to the start-up or first position. The centrifugal force in the first position moves the buffer out of the metering chamber, through a passage and into a first transfer trap. Similarly, centrifugal force in this position moves the liquid in the sample or blood separating chamber out the open end of the separating chamber, through a passage and into the first transfer trap. In the transfer trap there is partial mixing of the plasma and buffer.

The centrifugal device can then be accelerated to the spin speed. As this occurs, there is a translation of the planchette to the second position as centrifugal force moves the frame against the bias of the spring. As the planchette is moving to the second position, the centrifugal force vector is translated from the start-up or first vector to the second vector and the direction of the centrifugal force acting on the planchette is changed. Upon reaching spin speed, the partially diluted plasma passes through a mixing channel completely mixing the buffer and plasma. A fluid fill line is again developed by the centrifugal force trapping and holding the diluted plasma in a holding area. This holding area is at a predetermined location in the planchette such that the fluid fill line creates a barrier forcing excess fluid out of the holding area and into an overflow chamber thereby metering the diluted plasma to a predetermined volume. The fluid fill line also prevents flow of the diluted plasma out of the holding area.

The centrifuge device is then decelerated. As this occurs, the centrifugal force vector is translated from the spin speed position to the start-up or low speed position. Concurrently with this translation, centrifugal force is reduced resulting in the frame returning to the first position under the influence of the spring. The planchette is also translated from the second position to the first position. The centrifugal force acting along the start-up vector then moves the diluted plasma from the holding chamber into a reduction area that includes one or more reagents. The diluted plasma interacts with the reagent to provide a measurable response.

Using this assembly and method, the various steps necessary to perform chemical analyses are performed by a machine that can be programmed to perform different steps at preselected speeds for predetermined periods of time thus eliminating the need for time consuming manual operations. By translating the planchettes using centrifugal force, the frame of the assembly is simple in construction requiring few parts and minimizing the need for and the cost of servicing. In addition, since centrifugal force is employed to create fluid fill line barriers that move and hold the sample and buffer in the different chambers, a complex planchette requiring permanent physical barriers such as walls to control the flow of fluid is not required.

BRIEF DESCRIPTION OF THE DRAWINGS

Other and further objects, advantages and features of the invention will be apparent to those skilled in the art from the following detailed description thereof, taken in conjunction with the accompanying drawings in which:

FIG. 1 is a schematic illustration of an assembly for separating, metering, diluting and delivering fluid illustrated in a first or start-up position;

FIG. 2 is a schematic illustration similar to FIG. 1 illustrating the assembly for separating, metering, diluting and delivering a fluid in a second, spin position;

FIG. 3 is a elevational plan view of a planchette constructed in accordance with the principles of the present invention in the start-up or at-rest position;

FIG. 6 is a view of the planchette during acceleration subsequent to the deceleration illustrated in FIG. 5; and FIG. 7 is a view of the planchette during deceleration subsequent to the acceleration illustrated in FIG. 6.

DESCRIPTION OF THE PREFERRED EMBODIMENTS

Figure 4:
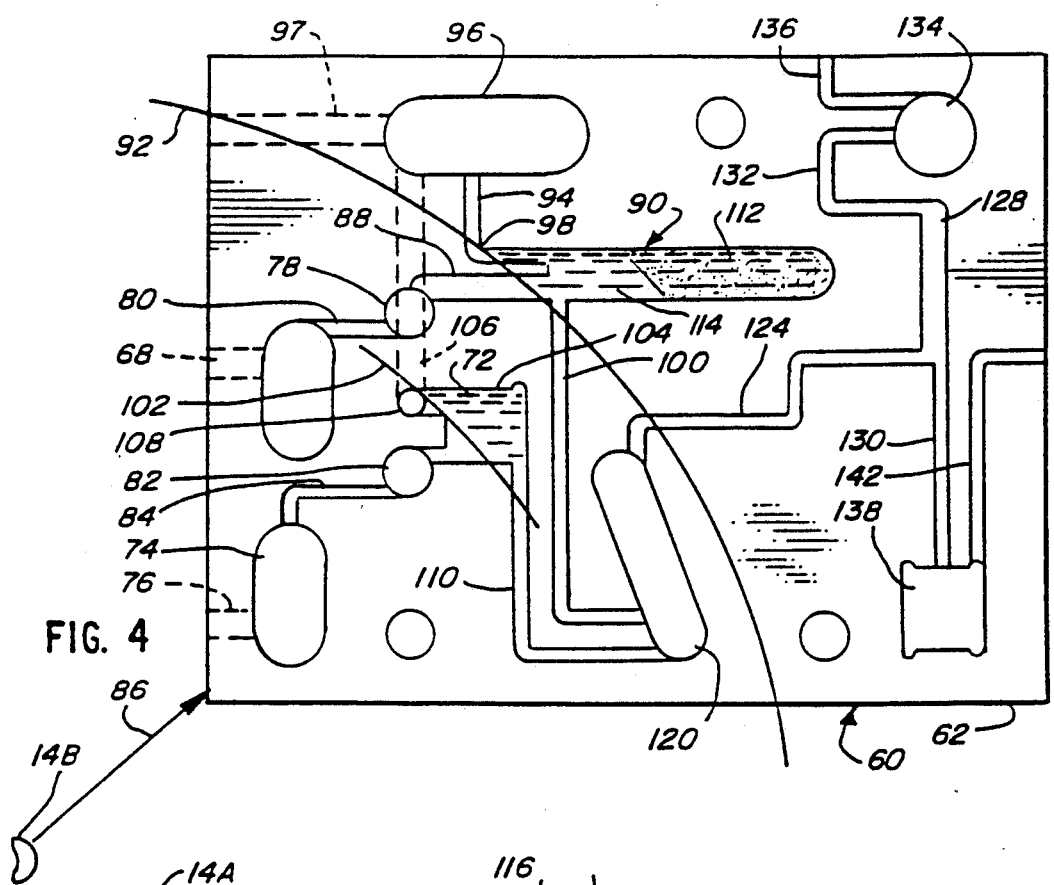
FIG. 4 is a view of the planchette illustrated in FIG. 3 translated from the position illustrated in FIG. 3 to the second position corresponding to the position illustrated in FIG. 2.

Medical and chemical analyses of liquid samples such as whole blood include many steps that are manually performed. Manually performing some or all of the steps is expensive and slow. Instruments for performing the necessary steps using centrifugal force are available; however, these instruments are complex and expensive, and servicing is difficult. The present invention allows analysis of a very small liquid sample of the order of a few microliters. This is of interest, particularly in medical analyses, since it allows the avoidance of subjecting a patient to drawing blood with syringes. Medical analyses, such as testing for the level of glucose in a patient's blood, often must be performed several times a day. Minimizing the amount of blood that must be taken for each test results in increased comfort to the patient and less reluctance to taking these tests.

To provide simplified and efficient testing, the present invention includes a new and improved centrifugal force generating assembly and a new and improved planchette. The centrifugal force generating assembly includes a centrifugally actuated frame that translates a planchette from a first position to a second position. In each position the planchette is aligned with a different centrifugal force vector. The planchette is of a design such that a fluid fill line is created by the interaction of centrifugal force and the fluids being analyzed in the planchette. The fluid fill lines provide barriers which prevent fluid flow in certain directions. By creating fluid fill lines, physical barriers required in prior art planchettes are eliminated and more precise metering of the fluids to be analyzed is possible.

Considering first the centrifugal force generating device or assembly, reference is made to FIGS. 1 and 2. A centrifugal force generating device or assembly generally designated by the reference numeral 10 is illustrated. The centrifugal force generating assembly 10 includes a rotating member 12 rotatable about a fixed spin axis 14 by a motor (not shown). The rotating member 12 is of a "S" configuration including an elongated central portion 16 with a first arm 18 and a second arm 20. First arm 18 terminates in a flat surface 22. Similarly, second arm 20 terminates in a flat surface 24.

To mount planchettes on assembly 10, a first planchette holding member 26 and a second planchette holding member 28 are provided. First planchette holding member 26 and second planchette holding member 28 are mechanically coupled to the rotating member 12 by a centrifugally actuated frame assembly generally designated by the reference numeral 30. As rotating member 12 approaches spin speed, the centrifugally actuated frame assembly 30 operates automatically to translate the first planchette holding member 26 and second planchette holding member 28 from a first, at rest or start-up position illustrated in FIG. 1 to a second, spin position illustrated in FIG. 2. As rotating member 12 is decelerated from the spin speed, frame assembly 30 automatically returns the first planchette holding member 26 and second planchette holding member 28 to the first position. The planchette holding members 26 and 28 are farther from the spin axis 14 in the second position than in the first position, and tend to seek the second position when acted upon by the centrifugal force produced when the assembly 10 is rotated. This action is used by the frame assembly 30 to translate the planchette holding members 26 and 28.

The centrifugally actuated frame assembly 30 includes a first frame member 32. A first end 34 of the first frame member 32 is pivotally secured to the first planchette holding member 26 by a pin 36. Similarly, a second end 38 of first frame member 32 is pivotally secured to the second planchette holding member 28 by a pin 40. As best illustrated by comparing FIGS. 1 and 2, first frame member 32 functions to guide the angular movement of first planchette holding member 26 and second planchette holding member 28 during the translation from the first position (FIG. 1) to the second position (FIG. 2) and from the second position to the first position.

The orientation of the first planchette holding member 26 and the second planchette holding member 28 relative to the spin axis 14 remains the same in the first position (FIG. 1) and in the second position (FIG. 2). By maintaining the same orientation, the centrifugal force vector acting on planchettes mounted on first planchette holding member 26 and second planchette holding member 28 can be changed to move fluid through the planchette. To maintain the same orientation and to prevent rotation of the first planchette holding member 26 relative to the spin axis 14, a second frame member 42 is provided. Second frame member 42 includes a first end 44 pivotally secured to the first planchette holding member 26 by a pin 46. A second end 48 of the second frame member 42 is pivotally mounted to the rotating member 12 by a pin 50. The connection of second frame member 42 to the rotating member 12 and the first planchette holding member 26 functions to guide the angular movement of the first planchette holding member 26 from the first position (FIG. 1) to the second position (FIG. 2). In effect, first planchette holding member 26 moves in an arc with a center at pin 50. The pivotal connection of both the first frame member 32 and the second frame member 42 to the first planchette holding member 26 prevents rotation of the first planchette holding member 26 relative to the spin axis 54. Consequently, the orientation of the first planchette holding member 26 relative to the spin axis 14 remains the same in both the first or second positions. To maintain the second planchette holding member 28 in the same orientation relative to the spin axis in both the first and second positions a third frame member 52 is pivotally secured to the second planchette holding member 28 and the rotating member 12 by pins 54 and 56, respectively.

While the centrifugal force generating assembly 10 is at rest and during start-up, the centrifugally actuated frame assembly 30 is biased to the first position (FIG. 1) by a resilient spring 58 attached to pins 46 and 54. Spring 58 holds frame assembly 30 in the first position until rotating member 12 reaches a predetermined spin speed. As spin speed is approached, the centrifugal force exceeds the force of spring 58 and the first planchette holding member 26 and second planchette holding member 28 seek the second position (FIG. 2) which is farther from the spin axis 14 than the first position.

In the second position a side of the first planchette holding member 26 engages the flat surface 22 and a side of the second planchette holding member 28 engage the flat surface 24. During the translation of the first planchette holding member 26 and the second planchette holding member 28, the orientation of the holding members is not varied relative to the spin axis 14 and the rotating member 12. Upon deceleration of the rotating member 12, the centrifugal force is reduced until the force of the spring 58 overcomes the centrifugal force swinging the first planchette holding member 26 and the second planchette holding member 28 to the first position (FIG. 1).

As will be understood by one skilled in the art, during rotation of the rotating member 12, centrifugal force vectors are developed that emanate radially outwardly from the spin axis 14. The first and second positions of the first planchette holding member 26 and the second planchette holding member 28 correspond to different angular positions around the spin axis 14 such that different centrifugal force vectors emanating from the spin axis 14 act upon the first planchette holding member 26 and second planchette holding member 28 in the first position and in the second position The two force vectors acting on the first planchette holding member 26 and the second planchette holding member 28 are illustrated by arrows in FIGS. 1 and 2. In FIG. 1, the arrow designated "Force Vector 1" illustrates the direction of centrifugal force acting on the first planchette holding member 26 and the second planchette holding member 28 in the first position. In the second position (FIG. 2), the centrifugal force acts alongaa vector in the direction designated by the arrow identified as "Force Vector 2."

By comparing FIGS. 1 and 2, it can be determined that in the second position the first planchette holding member 26 and the second planchette holding member 28 are at a greater radial distance from the spin axis 14 than at the first position and seek the second position when acted on by centrifugal force. By using centrifugal force, frame assembly 30 provides a simple structure for translating the first planchette holding member 26 and the second planchette holding member 28 to different angular positions resulting in different centrifugal force vectors acting on the planchette holding members.

To perform chemical and medical analyses using assembly 10, a planchette or processing chamber is mounted on the planchette holding members 26 and 28. By sequencing acceleration to spin speed and deceleration below the spin speed, this sequence, in combination with a specific design of planchette, will allow the centrifugal force generating device 10 to perform a number of different steps in a preferred medical or chemical analysis. By using centrifugal force and translating the planchette holding members 26 and 28 and a planchette, fluid fill lines are generated that replace the physical barriers required in prior art planchettes.

A planchette constructed in accordance with the principles of the present invention is illustrated in FIGS. 3–7 and generally identified by the reference numeral 60. To use assembly 10, planchettes 60 are mounted on both the first planchette holding member 26 and the second planchette holding member 28 in order for the assembly 10 to be balanced during rotation The location of cavities and passages in planchette 60 relative to the spin axis 14 is an important factor in the design of planchette 60. Planchette 60 is sensitive to its location relative to the spin axis 14 because centrifugal force developed by assembly 10 is employed to meter and move fluids through the different passages and chambers of the planchette 60, and to create fluid fill lines to hold fluid in the different chambers while a step of the analysis is being performed.

In one embodiment, planchette 60 is a onepiece, molded housing 62 with a transparent laminate sheet laminated on the top and/or the bottom of housing 62. This construction provides simplified assembly and reduces the expense of the planchette 60, which is important since planchette 60 is intended to be disposable.

To understand the construction of planchette 60 and the operation of assembly 10, both will be described by going through the steps of a chemical analysis on a sample of whole blood. Turning initially to FIG. 3, planchette 60 is illustrated in the "at rest" or start-up configuration corresponding to the first position of assembly 10 illustrated in FIG. 1. For illustration purposes only and not as an indication of exact positions, the location of spin axis 14 is illustrated by the circle 14A in FIG. 3 and the centrifugal force vector during start-up of assembly 10 is illustrated by the arrow designated by the reference numeral 64.

Prior to start-up of assembly 10, thirty to fifty microliters of whole blood 70 is introduced into a blood fill chamber 66 through a blood inlet port 68. The volume of the sample is not critical since the proper amount of blood to be used in the analysis is metered in a later stage of planchette 60. In addition, thirty to fifty microliters of buffer fluid 72 is introduced into a buffer fluid chamber 74 through a buffer fluid inlet port 76. With planchettes positioned on the first planchette holding member 26 and the second planchette holding member 28, assembly 10 is energized to spin rotating member 12. During acceleration, the centrifugal force vector acting on the planchette 60 corresponds to "Force Vector 1" in FIG. 1 and acts on planchette 60 in the direction of arrow 64 in FIG. 3. Once assembly 10 reaches a preselected spin speed, planchette holding members 26 and 28 are translated to the second position (FIG. 2) and the centrifugal force acting on planchette 60 in the second position is along "Force Vector 2."

As assembly 10 accelerates, there is not an instantaneous change from "Force Vector 1" (FIG. 1) to "Force Vector 2" (FIG. 2), but rather, a transition or translation. During this translation the centrifugal force is acting on the blood 70 in blood fill chamber 66 and the buffer 72 in the buffer fill fluid chamber 74 and it is undesirable for the blood 70 or buffer 72 to flow into the other stages of planchette 60 until the spin speed is reached To prevent flow of blood through planchette 60 prior to reaching the preselected spin speed, a start-up trap or fill fluid lock 78 is provided in an outlet passage 80 leading from the blood fill chamber 66. A similar start-up trap 82 is provided in the outlet passage 84 to the buffer fluid chamber 74. Start-up fluid traps 78 and 82 function to hold fluid flowing from chambers 66 and 74 during start-up and to prevent further movement of fluid into planchette 60 until full spin speed is reached.

Comparing FIGS. 3 and 4 of the drawings, the transition from start-up of assembly 10 to the spin velocity is illustrated. In FIG. 4 spin speed has been reached and the spin axis is schematically illustrated by the circle designated by the reference numeral 14B. Spin axis 14B corresponds to the relative position of the spin axis in the second position of assembly 10 (FIG. 2). At spin velocity, the direction of centrifugal force acting on planchette 60 is represented by the arrow 86. Centrifugal force acting along vector 86 moves whole blood through the start-up trap 78 and an inlet passage 88 into a plasma metering chamber 90 Contrary to the prior art, plasma metering chamber 90 has an unobstructed inlet. Blood is moved into plasma metering chamber 90 by centrifugal force that forms a fluid fill line schematically illustrated by the line 92. Fluid fill line 92 radiates outwardly from spin axis 14B. As blood flows into metering chamber 90, excess blood is forced into and through an overflow passage 94 and into an overflow chamber 96. To eliminate back-up pressure in overflow chamber 96, chamber 96 is vented to atmosphere by a vent passage 97. Flow of blood into overflow chamber 96 continues until fluid fill line 92 reaches the location defined by corner 98 in overflow passage 94. In this position of fluid fill line 92 the volume of blood in chamber 90 behind fluid fill line 92 has been predetermined by the size of chamber 92 and its position relative to spin axis 14B. In the present invention, the location and size of chamber 90 and the location of fluid fill line 92 perform the metering function. In one embodiment of the present invention the volume is 30 microliters.

Fluid fill line 92 functions as a barrier preventing flow of blood through overflow passage 94 once the desired amount has been metered in chamber 92. Once metering is complete, fluid fill line 92 also serves to prevent flow from the plasma metering chamber 90 through outlet passage 100 to another stage of planchette 60. Fluid fill line 92 allows planchette 60 to be constructed without physical barriers such as walls and similar structures partially covering the openings or mouths of different chambers such as plasma metering chamber 90. Such physcal barriers are necessary in the prior art to prevent and control the flow of fluid during rotation of the planchette relative to the centrifuge device. The fluid fill line 92 is unique in that it is removed upon deceleration of assembly 10, and the direction and location of the fill line can be moved by translation of the planchette 60 by frame assembly 30.

Simultaneously with the movement of blood into blood metering chamber 90, centrifugal force moves buffer fluid 72 from the buffer fill chamber 74 through the outlet passage 84 and the start-up trap 82 into a buffer metering chamber 104. Centrifugal force creates a second fluid fill line 102 radiating from spin axis 14B. As buffer fluid 72 is moved into the buffer metering chamber 104, excess buffer fluid 72 is forced into an overflow passage 106 through an inlet 108. As buffer fluid 72 flows into outlet 108, and through passage 106 to the overflow chamber 96, fluid fill line 102 moves radially outward from the spin axis 14B until it passes beyond outlet 108. At this point (FIG. 4) no further buffer fluid 72 can flow to the outlet 108 since the fluid fill line 102 acts as a barrier. Additionally, fluid fill line 102 prevents flow of buffer fluid 72 through an outlet passage 110. Fluid fill line 102 functions in a similar manner to fluid fill line 92 acting as a movable barrier and eliminating the necessity for a structural barrier to be included in the outlet passage 110, or in other portions of the buffer metering chamber 104.

Buffer metering chamber 104 is configured and is of a dimension such that the amount of fluid held in the buffer fluid chamber 104 by fluid fill line 102 is predetermined volume, thus metering the amount of buffer fluid 72. In one embodiment of the present invention, the volume of buffer solution that is metered by the buffer metering chamber 104 and held within this chamber by fluid fill line 102 is 15 microliters of buffer solution. As with chamber 90, the dimension of buffer fluid chamber 104 and its position relative to spin axis 14B determine the volume of buffer fluid 72 metered by chamber 104.

Figure 5:
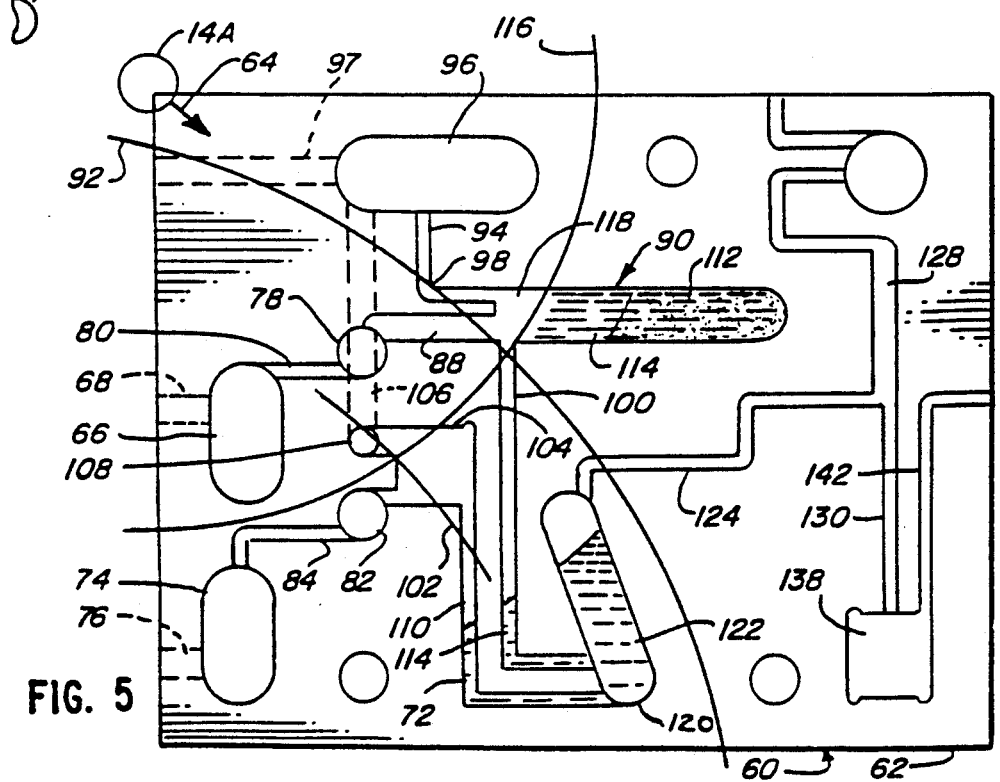
FIG. 5 is a view of the planchette during deceleration of the assembly returing the assembly to the position illustrated in FIG. 1.

Once the blood and buffer solution have been metered to the preselected volumes, assembly 10 continues to spin for a predetermined period to centrifuge the blood in blood metering chamber 90, separating red blood cells 112 from plasma 114. After the expiration of a predetermined period of time, separation of all of the red blood cells 112 from the plasma is accomplished. Assembly 10 can then be decelerated below the spin speed. As the speed decreases, the force of spring 58 overcomes the centrifugal force and returns frame assembly 30, first planchette holding member 26 and second planchette holding member 28 to the first position (FIG. 1). As this occurs, the spin axis returns to the position 14A (FIG. 5), and the centrifugal force vector acts along the line designated by the arrow 64 in FIG. 5 creating a new fluid fill line 116. Fluid fill lines 92 and 102 are illustrated in FIG. 5 for reference purposes illustrating the former positions of these fluid fill lines; however, during deceleration, fluid fill lines 92 and 102 do not exist.

Upon the removal of fluid fill lines 92 and 102, outlet passages 100 and 110 are no longer blocked and plasma 114 within the triangular area defined between fluid fill lines 92 and 116 designated by the reference numeral 118 is moved through outlet passage 100 into a holding area 120. The remaining plasma 114 in blood metering chamber 90 is held within chamber 90 by fluid fill line 116. The translation of the planchette 60 also removes fluid fill line 102 and centrifugal force moves the buffer solution 72 out of buffer metering chamber 104 through outlet passage 110 and into the holding area 120. In the holding area 120, plasma 114 and buffer solution 72 are partially mixed resulting in diluted plasma 122. Holding area 120 is at an angle relative to passage 100 and 110 such that during deceleration of assembly 10, the diluted plasma 122 does not travel up the side of holding area 120 and into another stage of planchette 60 until assembly 10 is again accelerated to spin speed.

Once diluted plasma 122 reaches holding area 120, assembly 10 is again accelerated to the preselected spin speed. As spin speed is reached, the planchette holding members 26 and 28 are translated to the second position and the force vector translates from vector 64 in FIG. 5 to vector 86 in FIG. 6. At the same time, frame assembly 30 translates first planchette holding member 26 and second planchette holding member to the second position (FIG. 2). During this translation, the diluted plasma 122 is moved up along the wall of the diluted plasma holding area 120.

Upon reaching the preselected spin speed, centrifugal force has moved the diluted plasma 122 through a mixing passage 124, thoroughly mixing the plasma and buffer, and into a diluted plasma area 128. A fluid fill line 126 functions as a barrier preventing flow of the diluted plasma 122 from area 128 down a reduction area passage 130. Diluted plasma area 128 is dimensioned to meter a preselected amount of diluted plasma 122. Excess diluted plasma 122 flows through an outlet passage 132 into an overflow chamber 134. To relieve back pressure, an air vent 136 communicates the overflow chamber 134 with the environment. Flow into chamber 134 continues until fluid fill line 126 moves to a corner 135 in passage 132. At this point, fluid fill line 126 prevents flow through passage 132 and the proper amount of diluted plasma 122 is held in area 128. The size of area 128 and its distance from spin axis 14B determine the position of fluid fill line 126 and thus the metered volume of diluted plasma 122 in area 128. During this step of the analysis, there is also a fluid fill line 92a that forms a barrier holding the plasma 114 and red blood cells 112 remaining within chamber 90 such that they do not flow through outlet passage 100.

Once the diluted plasma 122 has been metered in diluted plasma area 128, assembly 10 is decelerated below the spin speed removing the fluid fill line 126. As this occurs, the frame assembly 30 translates the planchette holding members 26 and 28 to the first position and the spin axis is translated from 14B (FIG. 6) to 14A (FIG. 7). During this translation, force vector 86 is translated to force vector 64 but centrifugal force is always acting on planchette 60 in the direction to the right as viewed in FIG. 7. This direction of centrifugal force moves diluted plasma 122 down a reduction area passage 130 while preventing flow into mixing passage 124. Diluted plasma 122 flows into a reduction area 138 and is held in reduction area 138 by a fluid fill line 140. To minimize back pressure in reduction area 138 as the diluted plasma 122 enters, an air vent 142 is provided that communicates reduction area 138 to the atmosphere or surrounding environment. The diluted plasma 122 will not flow out of the reduction area 138 through air vent 142 since the fluid fill line 140 acts as a barrier in the air vent 142.

The reduction area 138 can include a reagent or similar chemical that will react with the diluted plasma 122 providing a reaction that is monitored visually or by an instrument to determine the concentration of a selected chemical or chemicals in the diluted plasma 122. During this step of the analysis, a second fluid line 116A prevents the flow of plasma 114 through the outlet passage 100. In the reduction area 138 conventional dry-phase reagents or liquid-phase reagents can be used. One advantage of a dry-phase reagent is the allowance of room temperature storage of the planchettes 60.

The centrifugally actuated frame assembly 30 and the planchette 60 provide a system for metering and centrifuging whole blood to provide a metered amount of plasma. Buffer is also metered and mixed with plasma. The dilueed plasma in a known volume is then applied on a reagent area. Previously, these tasks were performed manually in a time-consuming, labor-intensive process. To accomplish the different processes on the fluid in assembly 10, however, a planchette is mounted on a centrifugally-actuated frame that operates automatically under the influence of centrifugal force to move or translate the planchette to different angular locations in relation to the spin axis of assembly 10.

Assembly 10 is a small-scale, bench top centrifugal analyzer capable of analyzing samples of blood or any other physioloical fluid. Sample measurement and distribution to individual testing areas as well as any required dilution is accomplished automatically within the confines of an integrally molded, single-use, plastic planchette 60. Assembly 10 is considerably smaller than existing centrifugal analyzers and considerably simpler mechanically. The planchettes 60 are designed to be disposable, yet contain all the reagents and compartments for sample volume metering and fluid and analytical measurement.

Many modifications and variations of the present invention are possible in light of the above teachings. Thus, it is to be understood that, within the scope of the appended claims, the invention can be practiced other than as specifically described.

What is claimed is:

1. A method for separating, metering, diluting and delivering a fluid, the steps coprising:
   rotating a processing member containing a fluid about a spin axis at a first rotational speed in a first angular position relative to said spin axis;
   accelerating said processing member to a second rotational speed; and
   translating said processing member to a second angular position farther from said spin axis than said first angular portion at said second rottional speed.

2. The method for separating, metering, diluting and delivering a fluid as claimed in claim 1 further comprising the steps of decelerating said processing member and translating said processing member to said first angular position.

3. A method for metring and centrigugation of whole blood and analyzing diluted plasma in a processing member, comprising the steps of:
   applying centrifugal force in a first direction on a processing member in a first position to move said processing member to a second position and cause whole blood to move from a first reservoir to a first chamber and buffer to move from a second reservoir into a third chamber;
   centrigruging said whole blood in said first chamber to separate red bolld cells from plasma;
   decelerating said processing member thereby causing said processing member to move to said first position angularly spaced from said second position and thereby move said plasma from said first chamber to a second chamber and move said buffer from said third chamber to said second chamber;
   applying centrifugal force on said processing member to again move said processing member to said second position and effect the mixing of said plasma with said buffer thereby diluting said plasma; and
   decelerating said processing member causing diluted plasma to move into a fourth chamber containing reagent and analyzing the resulting mixture in the fourth chamber.

* * * * *